US006858187B1

(12) United States Patent
Sipila et al.

(10) Patent No.: US 6,858,187 B1
(45) Date of Patent: Feb. 22, 2005

(54) APPARATUS FOR THE PREPARATION OF A RADIOACTIVE AQUEOUS SOLUTION

(75) Inventors: Hannu Sipila, Turku (FI); John Clark, Gerrads Cross (GB); Tom Wickstrom, Turku (FI); Henri Tochon-Danguy, Rosanna (AU)

(73) Assignees: Hidex Oy, Turku (FI); Oy Fluorplast AB, Petalax (FI)

( * ) Notice: Subject to any disclaimer, the term of this patent is extended or adjusted under 35 U.S.C. 154(b) by 0 days.

(21) Appl. No.: 09/959,718
(22) PCT Filed: May 9, 2000
(86) PCT No.: PCT/FI00/00408
§ 371 (c)(1), (2), (4) Date: Feb. 8, 2002
(87) PCT Pub. No.: WO00/68953
PCT Pub. Date: Nov. 16, 2000

(30) Foreign Application Priority Data

May 10, 1999 (FI) .................................................. 991066

(51) Int. Cl.⁷ .......................... G01N 23/00; G01N 37/00; G01T 1/164; G21G 1/10
(52) U.S. Cl. .................. 422/130; 250/363.03; 376/199; 376/201; 376/202; 422/81; 422/903; 436/56; 436/57
(58) Field of Search ................................. 204/265–266, 204/277–278; 205/335; 250/363.03; 376/199, 201, 202; 422/81, 130, 903; 436/56–57

(56) References Cited

U.S. PATENT DOCUMENTS 5,082,980 A * 1/1992 Berridge ...................... 568/917
5,482,865 A 1/1996 Ferrieri et al.

FOREIGN PATENT DOCUMENTS

EP 0 486 283 A2 5/1992

OTHER PUBLICATIONS

Jones, S. C. et al, Nuclear Medicine and Biology Advances, Proc. World Congr., 3rd (1983), Meeting Date 1982, vol. 2, 2120–2124, Editor: Raynaud, Claude, Publisher: Pergamon, Oxford, UK.*

Robinson, G. D. Jr. Et al International Journal of Applied Radiation and Isotopes 1985, 36, 425–428.*

Goodman, M. M. et al, Journal of Labelled Compounds and Radiopharmaceuticals 1991, 30, 166–168.*

Jackson, J. R. et al, Applied Radiation and Isotopes 1993, 44, 631–634.*

Bradley et al, "An Automated [$^{15}$O]$H_2O$ Production and Injection System for PET Imaging", *Nucl. Med. Biol.*,vol. 22, No. 2, 1995, pp. 24–249. (no month).

* cited by examiner

*Primary Examiner*—Arlen Soderquist
(74) *Attorney, Agent, or Firm*—Nixon & Vanderhye P.C.

(57) ABSTRACT

A device for preparing a radioactive water solution to be infused in a patient includes a reaction chamber (13) in which radioactive water vapour is formed by the catalysed reaction of oxygen gas containing oxygen-15 and hydrogen gas. A diffusion chamber (14) is provided which allows the radioactive water to penetrate, but which prevents the penetration of gasses. Tubes (26) and valves (16, 18) direct a sterile saline solution to the diffusion chamber (14), and then direct the saline solution containing radioactive water out from the diffusion chamber to a patient, or to a decay coil (22) being a part of the device. A measuring instrument is provided for measuring the radioactivity of the radioactive solution. The device is characterized in that the diffusion chamber (14), the tubes (26) the valves (16, 18), the radioactivity measuring instrument (17), and preferably also the reaction chamber 913), are mounted in the same frame 50, whereby they form a separate unit i.e. a water module (30), which as one entity can be detached from the lead shield (10) surrounding the device.

11 Claims, 3 Drawing Sheets

APPARATUS FOR THE PREPARATION OF A RADIOACTIVE AQUEOUS SOLUTION

This application is a National Stage Application of PCT/FI00/00408, filed May 9, 2000.

The object of the invention is a device for preparing a radioactive water solution to be infused in a patient.

Positron emission tomography (PET) is a quantitative, functional isotope imaging method used, for instance, for the examination of blood circulation in the human heart, brain or skeletal muscles. Water labelled with the short-lived (half-life 2.05 minutes) oxygen-15-isotope is used as the radioactive tracer. The radioactive water is administered as a physiological sodium chloride solution in water.

In order to examine a patient's blood circulation a radioactive solution will be infused, the solution comprises a physiological saline solution, in which radioactive water has been mixed, where oxygen is the radioisotope $15_O$ (oxygen-15). According to prior art such a solution is prepared in a device according to FIG. 1. Radio-active gas containing 1% oxygen and 99% nitrogen is supplied via the opening 11 in the lead shield of the device surrounded by the lead shield 10. A part of the total oxygen is non-radioactive oxygen, and a part is radioactive oxygen (oxygen-15). The radioactive gas is generated in a cyclotron. From a second opening 12 mixing gas is supplied into the device, the mixing gas containing 5% hydrogen and 95% nitrogen. By the catalyzed reaction of the hydrogen of the mixing gas with the oxygen of the radioactive gas in a reaction chamber ("oven") 13 radioactive water vapour is generated. The reaction is carried out in the presence of a palladium catalyst, the temperature is usually maintained at about 200° C. by electrical heating The gas coming from the reaction chamber 13 and containing radioactive water vapour is directed into a diffusion chamber 14 having a semi-permeable membrane (which usually is a dialysis membrane). A sterile saline solution is pumped via the opening 15 and the valve 16 into the diffusion chamber above the semi-permeable membrane. The radioactive water vapour penetrates the membrane and mixes into the sterile saline solution. Then the solution is directed to a Geiger-Muller counter 17 to measure the radioactivity, after which it is directed through the valve 18 and the opening 19 to the patient. The solution is administered intravenously into the patient for the PET examination. The valves 16 and 18 are three-way membrane valves. The reference numbers 20 and 21 represent filters. The radioactive water cannot be stored as the half-life of the oxygen-15 isotope is only 2.05 minutes, therefore it must be fresh when it is supplied to the patient. Patient examinations are not made continuously, but the operation of the cyclotron must be continuous.

Thus the preparation of the radioactive water is continuous, whereas its use is random. The waste production of radioactive saline solution is directed into a decay coil 22 for removal of the radioactivity, after which the solution is discharged via the opening 23. The gas which does not penetrate the membrane of the diffusion chamber is discharged from the device via the opening 24. The device is arranged in a lead shield in order to avoid irradiating the surrounding environment. The item number 25 shows a lead plug. The device which including its lead shield weighs several hundred kilograms is mounted under or on one side of the bed of the patient to be examined.

However, some disadvantages relate to the device described above. All tubes (26) and valves (16, 18) as well as the diffusion chamber are permanently mounted in the device. The device is installed in a lead chamber, which is quite heavy and thus difficult to move on wheels and cumbersome to open. The saline solution generated by the device and being dispensed must be sterile and free of pyrogens, and therefore the device must be tested for pyrogens each day. Further the device has a risk of virus contamination, because in principle an infection could get from the patient into the device as the result of a reverse flow.

The object of this invention is to provide an improved device for preparing a radioactive water solution intended for infusion in a patient, the device being easy to dismount and where the components coming into contact with the saline solution are easy to replace. A particular object is to provide a device where the sterility problems and the risk of contamination are eliminated. A further object is to provide a device where electrical safety is better than in known devices.

The characteristics of the invention appear in the claims. A device according to the invention is characterised in that the diffusion chamber, tubes, valves, radioactivity measuring instrument, and preferably also the reaction chamber, are mounted in the same frame and form a separate unit, i.e. a water module, which as one unit can be detached from the lead shield surrounding the device.

The invention is described in more detail with the aid of the following figures, in which FIG. 1 shows a device according to prior art;

Figure 1:
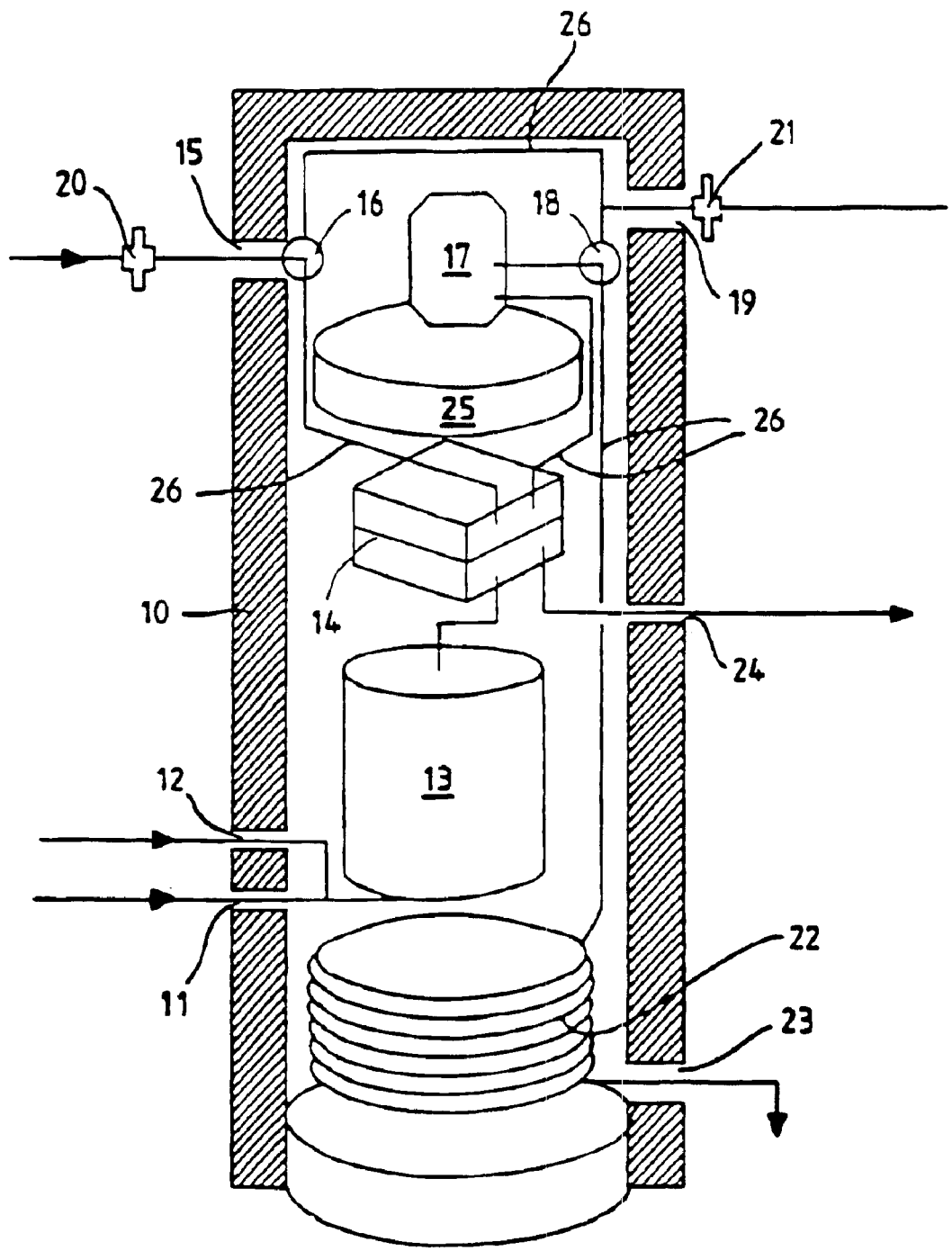
Figure 2:
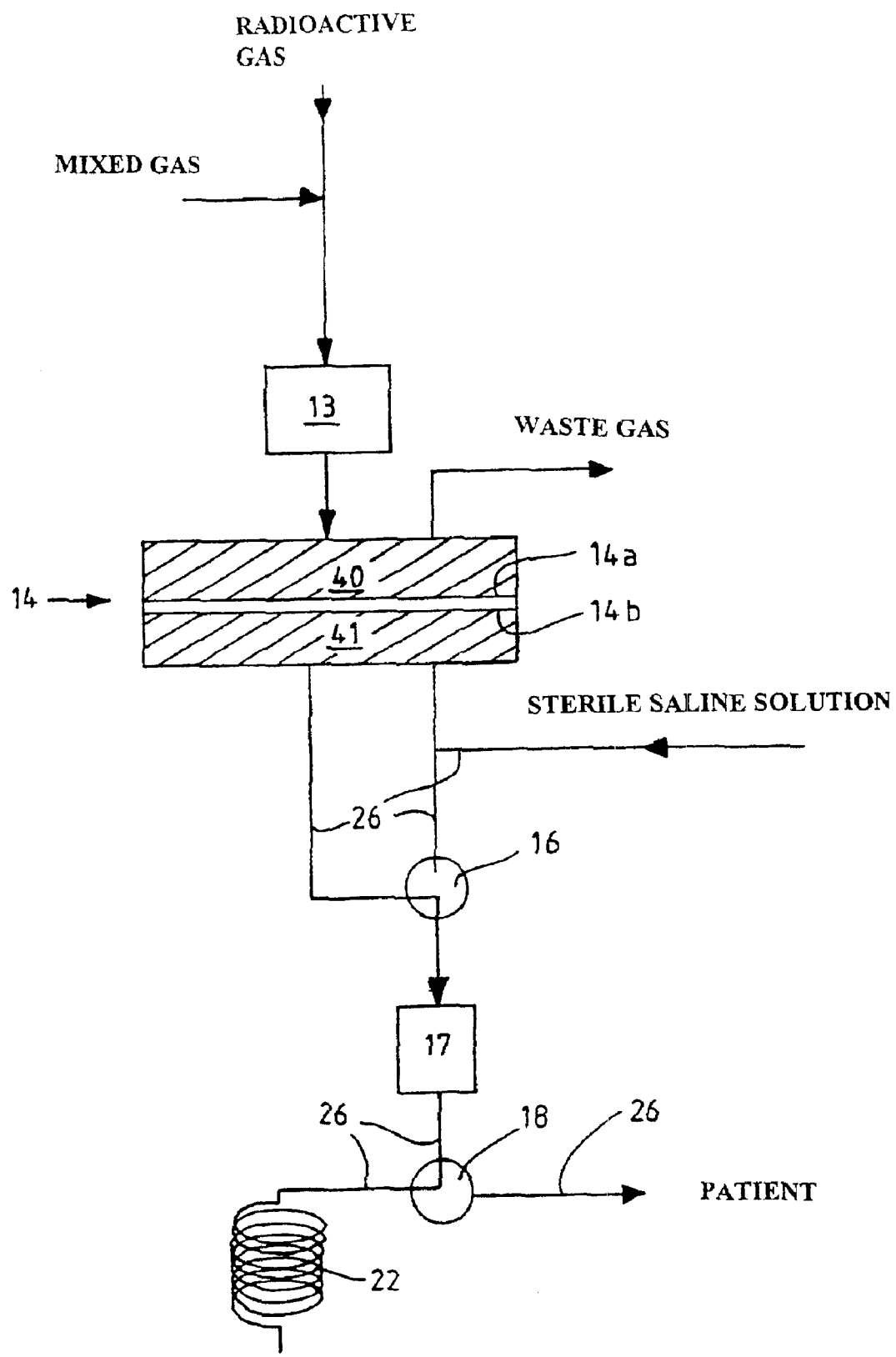
FIG. 2 shows a device according to the invention as a flow diagram.

FIG. 2 shows the different components of the device when they are connected to each other. The radioactive gas from the cyclotron containing 1% oxygen, a part of which is radioactive oxygen (oxygen-15), and 99% nitrogen, and a mixing gas containing 5% hydrogen and 95% nitrogen, are supplied to the reaction chamber 13 where the hydrogen and the oxygen undergo catalytic reaction in the presence of a $Pd/Al_2O_3$ catalyst to form water vapour. The temperature of the reaction chamber reaches 100 to 110° C., the heat being generated by the reaction of the oxygen and hydrogen. Due to this relatively low temperature the generation of ammonia is avoided. By using a smaller amount (300 mg) of a suitable catalyst (e.g. 1.0% Pd on alumina) radioactive water has been obtained at a yield which is 25 to 30% higher than in a conventional reaction chamber. The use of the previously predominant electrical heating of the reaction chamber with a resistor has been abandoned, and this has not reduced the yield of radioactive water. The reaction chamber 13 is connected to the diffusion chamber 14 by quick connects, in which case the distance between the reaction chamber and the diffusion chamber is very short (about 15 mm). The temperature of the reaction chamber is sufficiently high to keep the radioactive water generated in it in the form of steam when it enters the diffusion chamber. The diffusion chamber 14 has two membranes 14a and 14b, which separate the gas phase 40 from the liquid phase 41. The upper membrane 14a which is in contact with the gas phase 40 is a hydrophobic membrane (for instance of the type Millipore GV), and the lower membrane 14b which is in contact with the liquid phase 41 is a hydrophilic membrane (for instance of the type Millipore GS). Sterile sodium chloride solution is supplied by an infusion pump (not shown in the figure) to the solution side 41 of the diffusion chamber. The radioactive water vapour which has penetrated the membrane 14a will condense and mix with the sterile saline solution in the space between the membranes 14a and 14b of the diffusion chamber. The hydrophilic membrane 14b effectively prevents the penetration of gases, and they are discharged as waste gases. The radioactive saline solution is supplied via the valve 16 passed the photodiode 17 acting as a radioactivity measuring instrument, after which it is directed via the valve 18 to the patient, or to the decay coil 22, if there is no patient to be examined.

Figure 3A:
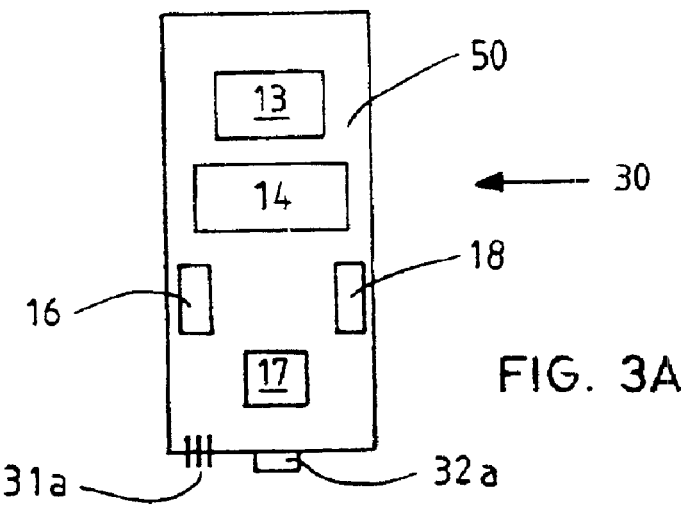
FIGS. 3A and 3B show the modular structure of a device according to one embodiment of the invention.
Figure 3B:
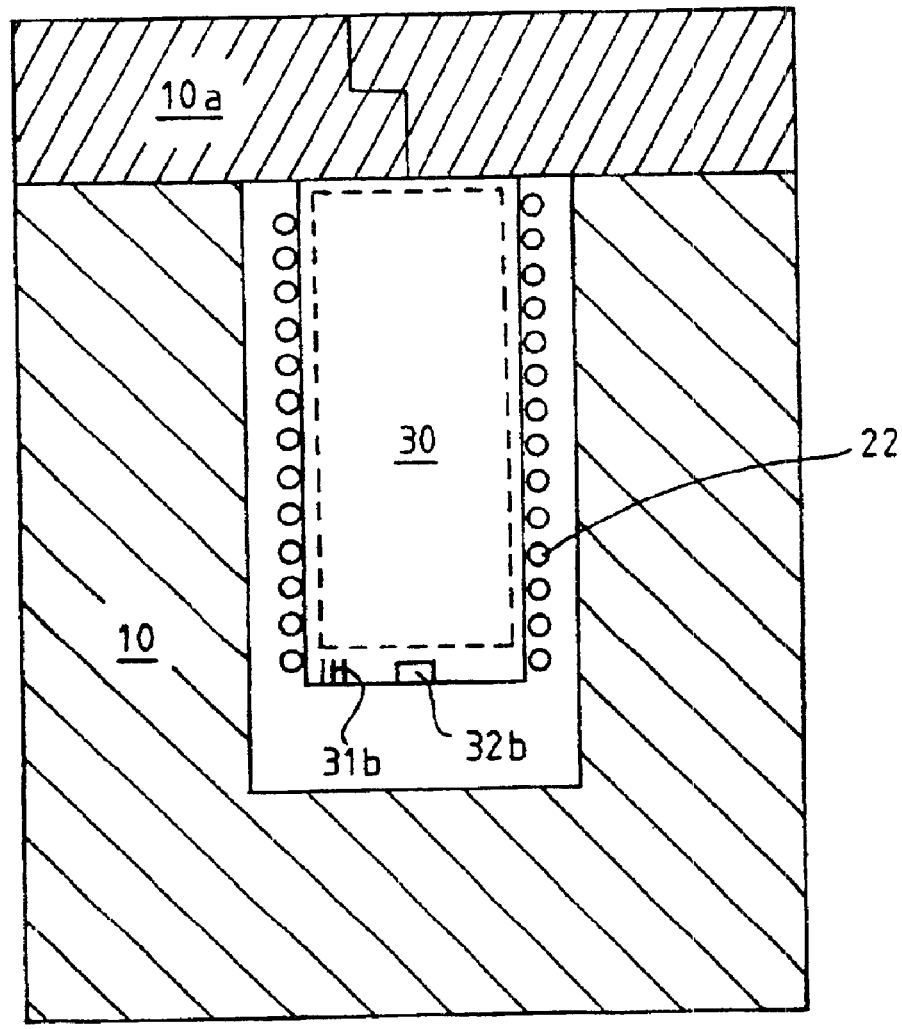

FIG. 3B shows in a cross section the structure of a device according to the invention. Within the lead shield 10 provided with an easily opened lid 10a there is a device which comprises a decay coil 22, into which a so called water module 30 can be inserted. Air cushions (not shown in the figure) are arranged under the lead shield, so that the equipment can be easily moved, even if it weighs several hundreds of kilograms. Preferably the lead shield 10 is provided with a small hole of about 20 mm diameter, to which a pipe is connected (not shown in the figure), which pipe could be connected to an extraction system. If there are any gas leaks from the device, such as leaks of unreacted hydrogen or radioactive gas, it is desirable that the lead shield be connected to an extraction system, so that these gases endangering safety can not spread into the immediate surroundings of the device.

The position of the water module 30 is marked with broken lines in FIG. 3B. In connection with the decay coil unit there are mounted quick release connectors "quick connects" 31b for the gases and for the waste liquid i.e. the liquid going to the decay coil. Further in connection with the decay coil unit there is an electric connector for the components of the water module which require electricity, such as for the valves 16 and 18 and the photodiode 17. FIG. 3A shows the water module 30 when it is detached from the lead shield 10 and the decay coil 22 of the device. The water module 30 comprises a frame 50, in which the following components are mounted in this solution: a diffusion chamber 14, tubes (not shown in the figure), valves 16 and 18, a radioactivity measuring instrument 17, and a reaction chamber 13. The water module 30 contains "quick connects" 31a for the gases at and for the liquid going to the decay coil (the waste liquid) and an electric connector 32a for the components of the water module requiring electricity. These connectors are connected to the connectors 31b and 32b in connection with the decay coil unit. The valves 16 and 18 are pinch valves or the like, which do not come into contact with the liquids flowing in the tubes.

Significant advantages are achieved with a module structure like this. As the diffusion chamber and the tubes transporting liquids are arranged in a separate module which can easily be detached from the lead shield, and as the valves are of the type which do not come to contact with the flows of liquid they direct, the diffusion chamber and the liquid tubes can be replaced after each patient treatment. The replaced components can be disposable, or they can be sterilised and reused. With this arrangement it can be ensured that the liquid delivered to the patient is sterile. The risk of contamination and the tests for pyrogens are avoided. Regarding the module structure it is most important that it comprises a diffusion chamber, valves, tubes and the radioactivity measuring instrument. As the reaction chamber is rather small, it can also easily be placed in the module, in the manner shown in FIG. 3A.

The electric safety of the device is substantially improved by abandoning the electric heating of the reaction chamber and by using a photodiode instead of a Geiger Muller counter as the detector of the radioactivity. The voltage required by a photodiode is 12 V, while the voltage required by a Geiger Muller counter is about 300V.

By using two membranes in the manner shown above it ensures that gas bubbles cannot get into the liquid to be infused.

The embodiments of the invention mentioned above are only examples of how the inventive idea can be realised. To a person skilled in the art it is obvious that different embodiments may vary within the scope of the claims presented below.

What is claimed is:

1. A device for preparing a radioactive water solution to be infused in a patient and which is adapted to be mounted detachably to a surrounding lead shield, the device comprising:
   a reaction chamber (13) within which radioactive water is capable of forming by catalytic reaction of hydrogen gas with radioactive oxygen-15 gas;
   a diffusion chamber (14) which allows the radioactive water to penetrate, but which prevents the penetration of gases;
   tubes (26) and valves (16, 18) for directing a sterile saline solution to the diffusion chamber (14), and for directing the saline solution containing radioactive water out from the diffusion chamber;
   a measuring instrument (17) for measuring the radioactivity of the radioactive solution, and
   a frame (50) for commonly mounting at least the diffusion chamber (14), the tubes (26), the valves (16, 18) and the radioactivity measuring instrument (17), to form a separate water module unit (30), which as one entity is capable of being detached from the lead shield (10) surrounding the device.

2. A device according to claim 1, further comprising a decay coil (22), wherein the water module unit (30) is separable from the decay coil (22).

3. A device according to claim 2, wherein water module unit (30) and the decay coil (22) comprise mateable quick release connectors (31a, 31b) for the gases and the liquid directed from the water module unit (30) to the decay coil (22), and an mateable electric connectors (32a, 32b) for the components of the water module unit requiring electrical supplies.

4. A device according to claim 1, wherein the tubes (26) of the water module unit (30) conveying the saline solution to the diffusion chamber (14) are replaceable after each patient examination, and wherein the valves (16, 18) are pinch valves which do not come into contact with liquids flowing in the tubes.

5. A device according to claim 1, wherein the diffusion chamber (14) comprises two membranes (14a, 14b) located on respective gas and saline solution sides thereof, wherein a first one of the membranes (14a) is a hydrophobic membrane located on the gas side (40), and a second one of the membranes (14b) is a hydrophilic membrane located on the saline solution side (41).

6. A device according to claim 1, wherein the radioactivity measuring instrument (17) comprises a photodiode.

7. A device according to claim 1, wherein the reaction chamber (13) is a small-size reaction chamber operating exclusively with the aid of the heat of the reaction between oxygen and hydrogen.

8. A device according to claim 1, wherein the frame (50) also commonly mounts the reaction chamber (13) as part of the water module unit.

9. A system for providing a radioactive water solution to be infused in a patient comprising a device in which the radioactive water solution is prepared, and a lead shield (10) which surrounds the device, wherein the device comprises:

a reaction chamber (13) within which radioactive water is capable of forming by catalytic reaction of hydrogen gas with radioactive oxygen-15 gas:

a diffusion chamber (14) which allows the radioactive water to penetrate, but which prevents the penetration of gases;

tubes (26) and valves (16, 18) for directing a sterile saline solution to the diffusion chamber (14), and for directing the saline solution containing radioactive water out from the diffusion chamber to a patient or to a decay coil (22)

a measuring instrument (17) for measuring the radioactivity of the radioactive solution, and a frame (50) for commonly mounting at least the diffusion chamber (14), the tubes (26), the valves (16, 18), and the radioactivity measuring instrument (17), to form a separate water module unit (30), which as one entity is detachably mounted to the lead shield (10) surrounding the device; and wherein the lead shield (10) of the device is provided with a lid (10a) which can be easily opened.

10. A device system according to claim 9, further comprising are cushions which are arranged under the lead shield (10).

11. A system according to claim 9, the lead shield (10) a hole and a tube connected to the hole, wherein the tube is connectable to a suction source.

* * * * *

UNITED STATES PATENT AND TRADEMARK OFFICE
CERTIFICATE OF CORRECTION

PATENT NO.     : 6,858,187 B1
DATED          : February 22, 2005
INVENTOR(S)    : Sipilä et al.

It is certified that error appears in the above-identified patent and that said Letters Patent is hereby corrected as shown below:

Column 4,
Line 39, delete the word "an" after the word "and";

Column 6,
Line 8, delete the word "device" before the word "system"; and
Line 9, change "are cushions" to -- air cushions --.

Signed and Sealed this

Ninth Day of August, 2005

JON W. DUDAS
*Director of the United States Patent and Trademark Office*